(12) United States Patent
Sykes

(10) Patent No.: US 6,301,971 B1
(45) Date of Patent: Oct. 16, 2001

(54) APPARATUS FOR TESTING THE INTEGRITY OF A BOND

(75) Inventor: Robert Sykes, Tendring (GB)

(73) Assignee: Dage Precision Industries, Inc., Buckinghamshire (GB)

(*) Notice: Subject to any disclaimer, the term of this patent is extended or adjusted under 35 U.S.C. 154(b) by 0 days.

(21) Appl. No.: 09/196,832

(22) Filed: Nov. 20, 1998

(30) Foreign Application Priority Data

Nov. 20, 1997 (GB) .................................................. 9724458

(51) Int. Cl.[7] .................................................. G01N 3/08
(52) U.S. Cl. .................................................. 73/827
(58) Field of Search .................. 73/862.638, 862.639, 73/862.584, 827, 812, 850, 852–854, 105; 356/244, 213, 4, 531, 909, 5, 774, 209

(56) References Cited

U.S. PATENT DOCUMENTS

| 4,243,360 | * | 1/1981 | Wright | 416/191 |
|---|---|---|---|---|
| 4,458,865 | * | 7/1984 | Sandorff | 244/134 R |
| 4,501,398 | * | 2/1985 | Sandorff | 244/134 R |
| 5,633,455 | * | 5/1997 | Quate | 73/105 |
| 5,646,338 | * | 7/1997 | Mercusot et al. | 73/86 |
| 5,807,758 | * | 9/1998 | Lee et al. | 436/526 |
| 5,886,268 | * | 3/1999 | Larsson | 73/862.583 |
| 5,892,157 | * | 4/1999 | Syr'e | 73/812 |
| 6,078,387 | * | 6/2000 | Sykes | 356/244 |

* cited by examiner

Primary Examiner—Benjamin R. Fuller
Assistant Examiner—Abdullahi Aw-Musse
(74) Attorney, Agent, or Firm—Kilpatrick Stockton LLP

(57) ABSTRACT

Apparatus for testing electrical wire bonds of semiconductor devices includes two unequal length cantilever arms (14a, 14b) on a baseplate (11) and a test head (15) at the free end of the arms. The arrangement ensures substantially frictionless straight line movement of a test hook (32) on the text head over the range of deflection expected. A pneumatic or magnetic (21, 22) frictionaless damper is disclosed. The test hook (32) may be orientated by a stepper motor (35) of the test head.

10 Claims, 3 Drawing Sheets

APPARATUS FOR TESTING THE INTEGRITY OF A BOND

This invention concerns a device for testing the integrity of a bond between a semiconductor device and an electrical conductor thereof.

Semiconductor devices are small, typically from 0.2 mm square to 15 mm square. Around the edge of the semiconductor substrate numerous sites for the bonding of electrical conductors are provided, these sites are very small and typically about 0.05 mm wide and 0.1 to 0.7 mm apart. Very thin wires, usually about 0.025 mm in diameter, are bonded to respective sites, and connect these sites to associated electrical circuitry and components. It is necessary to test bond integrity at the sites in order to gain confidence that the bonding method is adequate and that the bond strength is sufficient. Difficulties arise because of the very small dimensions of the components, the precision with which the testing device must be positioned, and the very small forces and deflections which are to be measured.

A known test device has a tool, such as a miniature hook or tweezers, for engagement with the wire at a bond site. In practice the semiconductor substrate is restrained and the wire is pulled by the tool to test the bond strength in tension. A force transducer is incorporated in the device to measure the force necessary to break or non-destructively test the bond or wire, as the case may be.

The forces measured by the device are very small. Often these forces are of a similar order to friction and stiction forces within the test device itself, and accordingly great care is taken to reduce the effect of these forces as much as possible. Nevertheless, prior art testing devices inevitably suffer from small but significant variations in measured force due to the inconstant internal friction of bearing components, hysteresis and the like.

Another difficulty is that the movement of the tool must be carefully controlled to avoid a sideways component as the bond breaks, which might damage an adjacent bond or wire, or which might render calculation of the bond strength more difficult.

A further requirement is that sequential tests be undertaken with the minimum of delay. Accordingly the device should re-zero as quickly as possible so as to give maximum productivity.

A typical prior test device utilizes a tool at the tip of a cantilever arm, the arm having a strain gauge thereon to measure the applied load. The tip of such an arm inevitably moves in an arc, and this device is thus undesirable because a purely linear pull is not possible, and because the arcuate movement may result in collision with another wire or bond site. The danger of collision damage is particularly acute if the bond or wire should break suddenly when under load.

A parallelogram linkage has been proposed to ensure movement of the tool in an approximately straight line, but such a linkage retains a degree of sideways movement, and the pivot points of the linkage introduce extra sources of friction which, as noted above, are undesirable.

The present invention has been developed to take into account the aforementioned difficulties, and provide a frictionless test device which substantially eliminates the sideways component of tool movement.

According to the invention there is provided apparatus for testing the integrity of a bond between a semi conductor device and an electrical conductor thereof, the apparatus comprising a baseplate having two cantilever arms extending therefrom in substantially the same direction, a test head operatively fixed to the free ends of said arms, and measurement means to measure the force deflection characteristic of said arms on movement of said test head relative to said baseplate in the plane of said arms, wherein said arms are of unequal effective length, the test head having a test datum on one side of the arm with longer effective length, the arm with the shorter effective length being on the other side of the arm with the longer effective length, and the apparatus being proportioned such that a small deflection of said arms results in movement of said test datum substantially perpendicularly to the direction of extension of said arms.

Although configurations with convergent or divergent arms are possible, the geometry of movement is rather complex. Accordingly in the preferred embodiment the arms are substantially parallel and of unequal length, and the test head extends substantially orthogonally to the arms.

The unequal length cantilever arms ensure that the test datum can much more nearly follow a straight line over the test deflection, typically an order of magnitude better than prior art parallelogram linkage. In a preferred embodiment a typical deviation of 0.0005 mm is achievable over a deflection of 3.5 mm in a test head having the short arm about two thirds of the length of the long arm, and the test datum about the same distance away from the long arm. In contrast a typical equal length beam arrangement having a similar geometry and two long arms would have a deviation of 0.1 mm over the same deflection.

The cantilever arms may be machined from aluminium and be of appropriate dimensions to remain within their elastic range over the anticipated deflection of the test datum.

Preferably the apparatus includes a non-contact damping device, such as a pneumatic or magnetic damper, which can damp relative movement of the test head to permit rapid re-zero of the device. In a preferred embodiment the damper is of appropriate dimensions to ensure effective damping within 5 cycles.

The test head may include a rotatable shaft to permit the angular position of the test datum to be varied; such a modification is useful for orientation of a hook. A co-axial stepper motor is preferably provided to rotate the shaft.

According to another aspect the invention provides test apparatus having no moving parts and comprising a baseplate, two unequal length cantilever arms extending therefrom in substantially the same direction, and a test head operatively fixed to the free ends of said arms, the arms being substantially parallel and the test head being movable relative to said baseplate by resilient movement of said arms. Such apparatus eliminates the internal friction inherent in prior art linkage-type test devices.

Other aspects of the invention will be apparent from the following description of a preferred embodiment shown by way of example only in which.

Figure 2:
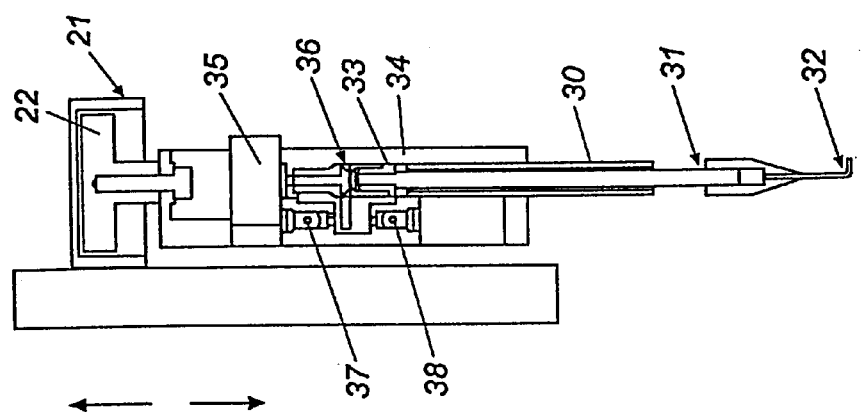
FIG. 2 is a transverse section on line 2—2 of FIG. 1.

With reference to the drawings, a test head 10 comprises a base plate 11 having a fixed mass 12 mounted thereon by screws 13. Upper and lower cantilever arms 14a, 14b extend in parallel from the mass 12 and terminate at their free ends in a moving mass 15. The upper arm 14*a* is somewhat shorter than the lower arm 14*b*, as illustrated.

The moving mass 15 is able to move up and down within limits imposed by the resilient return forces exerted by the arms 14*a*, 14*b*. The fixed mass, arms and moving mass may be of e.g. aluminium.

An air dashpot assembly 20 is provided at the upper end of the moving mass and comprises an upturned cylindrical chamber 21 attached to the base plate 11 and a piston 22 attached to the moving mass 15 in the vicinity of the free end of the upper arm 14*a*. The piston 22 is a close fit in the chamber 21 but does not touch the chamber wall. As is well known, the dashpot will permit friction free movement of the moving mass at low speed, but will damp high speed movement by virtue of the small clearance between the piston 22 and the wall of chamber 21. The diameter and depth of the piston, and the clearance are selected by conventional techniques to give a desired damping effect according to the operating parameters required.

Typically an undamped moving mass may oscillate several hundred times before coming to rest and allowing the device to re-zero for the next test. With appropriate attention to the dimensions, the dashpot assembly 20 can reduce the number of oscillations to less than 5 before re-zero of the device can occur.

A cylindrical sleeve 30 extends downwardly from the moving mass 15 and contains a pull shaft 31 to the end of which is attached a test tool 32 such as a hook (as illustrated), tweezers or some other suitable device.

The upper end of shaft 31 has a collar 33 which rests on a shoulder 34 of the moving mass. The shoulder 34 defines an abutment whereby movement of the moving mass is transferred to the shaft 31 during testing, and thereby to the hook 32.

The uppermost end of the shaft 31 is coupled to an electric stepper motor 35 which can in use be energised to rotate the shaft by a predetermined angular amount. A pin 36 extends radially from the shaft 31 and, once per revolution, interrupts a beam between a photo-electric emitter 37 and receiver 38. The pin 36 thus acts as a datum sensor, and in conjunction with the stepper motor 35 enables the orientation of the tool 32 to be selected.

One or both cantilever arms has a strain gauge 51 mounted thereon and calibrated to give a load/deflection characteristic for the moving mass 15.

A projection 61 of the baseplate is a loose fit in an aperture 62 provided in a web of the test head, and serves to restrict movement of the test head to a distance which maintains the arms 14*a*, 14*b* within their elastic range.

As is clear from FIG. 2, the moving mass 15 is spaced from the baseplate 11 and can thus move without friction. Deflection of the moving mass results in a proportional increase in return load imposed by the cantilever arms 14*a*, 14*b*. As noted above, provided the speed of movement is low the dashpot assembly has a negligible effect.

In use the base plate 11 is connected to a multi-axis drive which permits the test head 10 to be moved in three dimensions. The test head is manoeuvred to the test position, and the tool 32 orientated for engagement with the component to be tested.

Figure 1:
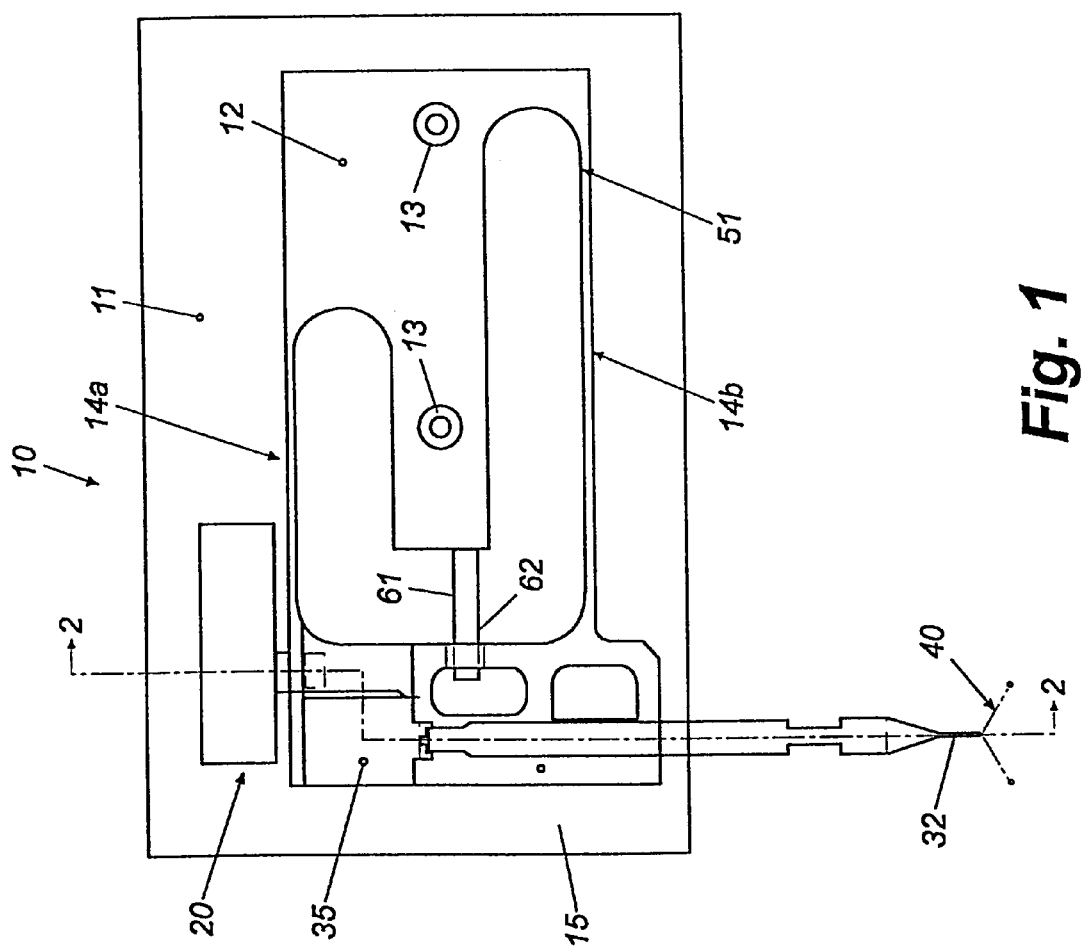
FIG. 1 is a side elevation of a test cartridge incorporating the invention.

Upward movement of the test head engages the tool with the component to be tested; a wire 40 is illustrated in FIG. 1. Increasing load results in deflection of the moving mass downwards. The value of the increasing load on the test wire can be calculated from the characteristic of the strain gauge. Movement of the moving mass is free of friction, and thus the load at the test tool can be determined with great accuracy.

At the point when the test piece breaks, the moving mass will tend to move rapidly upwardly and oscillate. This rapid movement is immediately damped by the dashpot 20, and thus allows the output from the strain gauge to be re-zeroed within a short period of time, typically less than one second.

Figure 4:
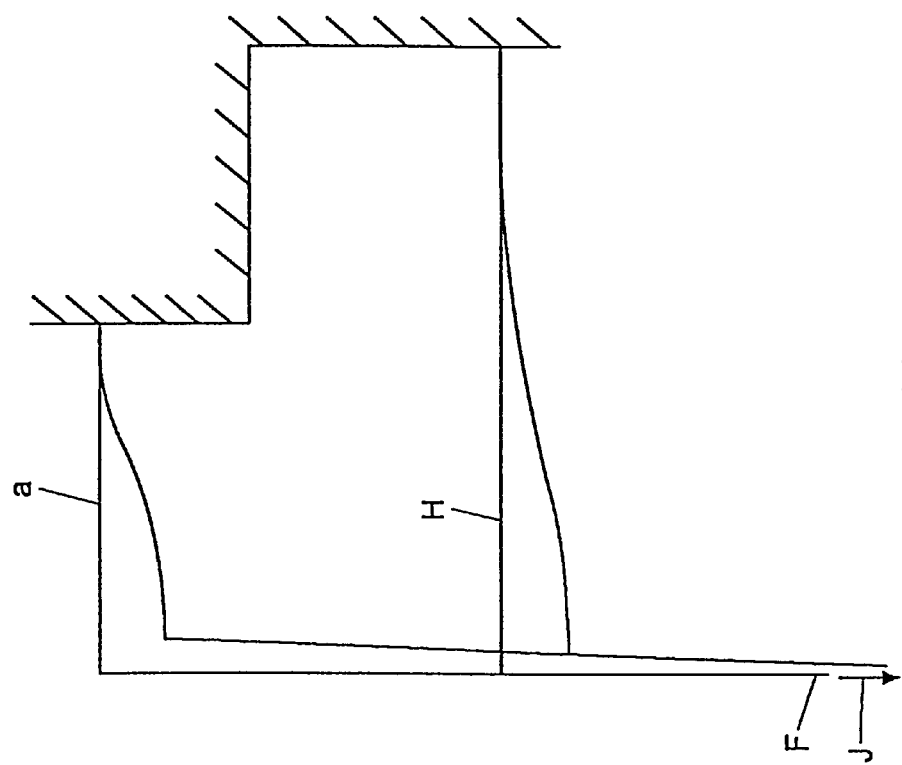
FIG. 4 shows the path of movement of a test head according to the present invention.

As a result of the unequal length of the arms 14*a*, 14*b*, the test tool 32 follows a straight line path over the likely range of deflection of the test component prior to breakage. This effect is illustrated in FIGS. 3 and 4.

Figure 3:
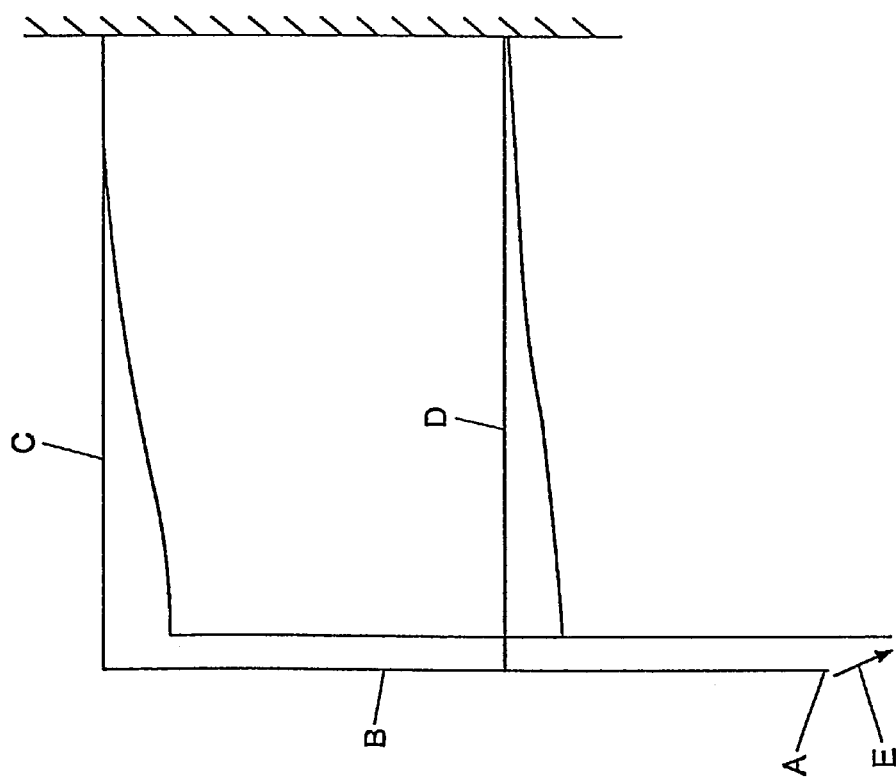
FIG. 3 shows the path of movement of a test head having equal length cantilever arms.

FIG. 3 shows the path of movement of a test tool A attached to a test head B having equal length cantilever arms C, D. The sideways component of movement as the arms change-effective length can be clearly seen, and is represented by arrow E. FIG. 4 shows the path of movement of a test head F according to the present invention. The unequal length arms G, H permit movement in the substantially straight line represented by arrow J.

Thus the device provides a truly elastic, friction free mechanism which constrains the test tool to travel in a path of minimum curvature which, over the small deflection expected, equates to a straight line. The device also provides friction free damping to prevent free oscillation of the moving mass at higher speeds. In a specific embodiment arms having lengths of 74 mm and 41 mm exhibited a deviation of 0.0005 mm from a straight line over a deflection of 3.5 mm. A mechanism having equal length beams of 74 mm would show a deviation of about 0.1 mm over the same deflection. Thus, the deviation of the inventive arrangement is at least an order of magnitude better than an equal length beam arrangement, and the friction inherent in a parallelogram linkage is avoided. For test devices of this kind, sideways deviation in excess of 0.0005 mm would have an effect on performance and accuracy, and thus the apparatus of the present invention is a major improvement.

Figure 6:
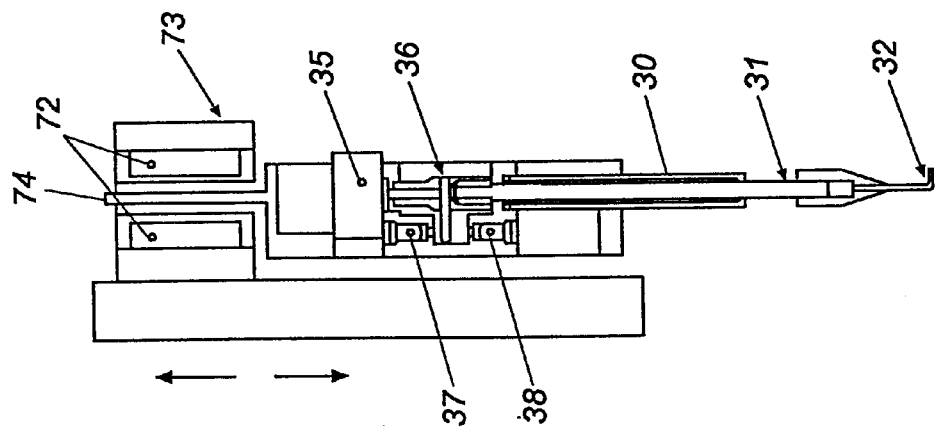
FIG. 6 is a transverse section on line 6—6 of FIG. 5.
Figure 5:
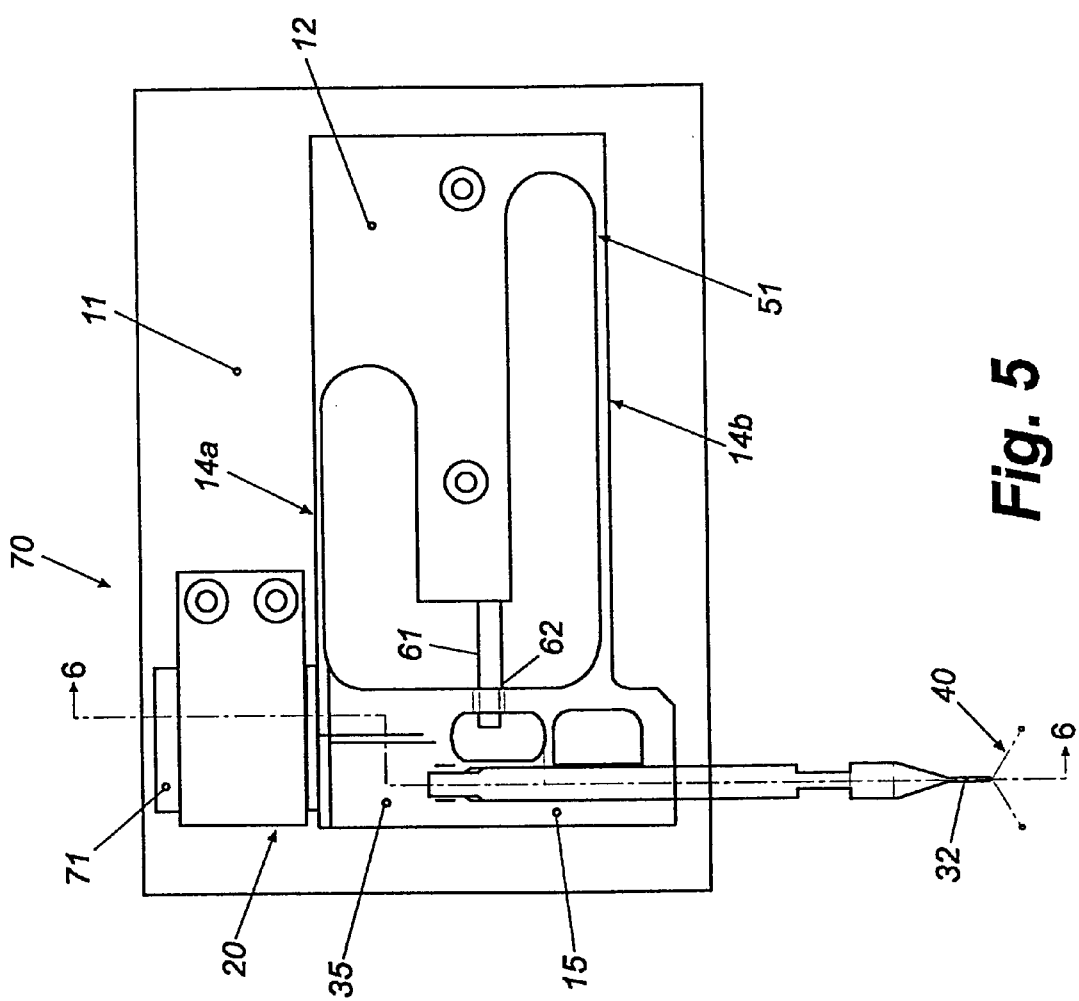
FIG. 5 is a side elevation of an alternative test cartridge incorporating the invention.

An alternative embodiment is illustrated in FIGS. 5 and 6 and comprises a test head 70 having an alternative damper 71. The remaining components are the same as in the first embodiment and carry common reference minerals.

The damper 71 comprises one or more permanent magnets 72 mounted in a housing 73 attached to the base plate 11. A vane 74 attached to the upper end of the moving mass 15 is located centrally within an aperture defined within the magnets 72. In operation the permanent magnets 72 induce eddy currents in the vane 74 which resist movement of the vane and which are proportional to the velocity of the vane. Accordingly the damping force is proportional to the velocity of the vane, and at low velocity is negligible. However the high velocity which may occur, on breakage of a test component under load, is strongly damped.

One advantage of the second embodiment is that for a similar damping effect, tolerances can be more generous, and accordingly the difficulties of both manufacture and assembly are eased.

Active damping is envisaged where it is desired to reduce the time to re-zero to an absolute minimum. Such a feature may be particularly important in a fully automatic test machine. Active damping may for example be achieved by sensing displacement of the test head, and applying a current to field coils surrounding the vane 74. In this way the damping effect can be varied by changing the magnetic restorative force in proportion to the displacement of the test head from the rest position.

Several test heads may be provided, with the cantilever arms designed to impose pull forces of e.g. 100 g, 1 kg and 10 kg whilst remaining elastic within the expected deflective range; the width and thickness of the arms are designed appropriately. The strain gauge 51 is typically applied to the arm 14b so as to compensate for the actual mass of the moving mass 15, and thus show approximately zero strain in the free condition.

What is claimed is:

1. Apparatus for testing integrity of a bond between a semiconductor device and an electrical conductor thereof, the apparatus comprising a baseplate having two cantilever arms in a plane and extending from the baseplate in substantially a same direction and having free ends, a moving mass fixed to the free ends of said arms and supported solely thereby, and measurement means to measure a force deflection characteristic of said arms on movement of said moving mass relative to said baseplate in the plane of said arms, wherein said arms are of unequal length, the moving mass having a test datum on one side of a longer of said arms, a shorter of said arms being on another side of the longer arm, and the arms being proportioned such that a small deflection of said arms results in movement of said test datum essentially perpendicular to the direction of extension of said arms.

2. Apparatus according to claim 1 wherein said arms are substantially parallel, and said moving mass extends substantially orthogonally to the arms.

3. Apparatus according to claim 1, wherein said arms are integral and of aluminum.

4. Apparatus according to claim 1 and further including a non-contact damping device to damp relative movement of said moving mass.

5. Apparatus according to claim 4, wherein said damping device is pneumatic.

6. Apparatus according to claim 4, wherein said damping device is magnetic.

7. Apparatus according to claim 1 wherein said moving mass includes a rotatable shaft to permit the angular position of said test datum relative to said arms to be varied.

8. Apparatus according to claim 7 and further including an axial stepper motor to rotate said shaft.

9. Apparatus according to claim 1 wherein said test datum is defined by a hook on said moving mass.

10. A test device for testing integrity of a bond between a semiconductor device and an electrical conductor thereof, the test device comprising a baseplate, two cantilever arms of unequal length extending therefrom in substantially a same direction, and a moving mass fixed to free ends of said arms and supported solely thereby, the arms being substantially parallel and the moving mass being movable relative to said baseplate by deflection of said arms in response to force from engagement of the electrical conductor so that a small deflection of said arms results in movement of said moving mass essentially perpendicular to the direction of extension of said arms wherein the force producing said deflection is measured.

* * * * *